United States Patent [19]

Halpern et al.

[11] Patent Number: 4,888,139
[45] Date of Patent: Dec. 19, 1989

[54] PROCESS FOR PREPARING $CHF_2OCHFCF_3$ AND $CHF_2OCHClCF_3$ AND NOVEL INTERMEDIATE COMPOUNDS EMPLOYED THEREIN

[75] Inventors: Donald F. Halpern, Fanwood; Mark L. Robin, South Plainfield, both of N.J.

[73] Assignee: BOC, Inc., Murray Hill, N.J.

[21] Appl. No.: 301,684

[22] Filed: Jan. 25, 1989

Related U.S. Application Data

[62] Division of Ser. No. 220,129, Jul. 18, 1988, Pat. No. 4,855,511.

[51] Int. Cl.$^4$ .................. C07C 53/40; C07C 53/48
[52] U.S. Cl. .................................................. 562/840
[58] Field of Search ............................... 260/544 X

[56] References Cited

U.S. PATENT DOCUMENTS 4,542,238  9/1985  Ishikawa ..................... 260/544 X Primary Examiner—Howard T. Mars
Attorney, Agent, or Firm—R. Hain Swope; Larry R. Cassett

[57] ABSTRACT

Process for preparing $CHF_2OCHFCF_3$ through the use of novel intermediate compounds $CHCl_2OCH_2COCl$ and $CHCl_2OCHClCOCl$.

2 Claims, No Drawings

PROCESS FOR PREPARING $CHF_2OCHFCF_3$ AND $CHF_2OCHClCF_3$ AND NOVEL INTERMEDIATE COMPOUNDS EMPLOYED THEREIN

This is a division of application Ser. No. 220,129 filed July 18, 1988 now U.S. Pat. No. 4,855,511.

FIELD OF THE INVENTION

The present invention is directed to the field of inhalation anesthetics and particularly to methods of producing known volatile liquid inhalation anesthetics from inexpensive starting materials.

BACKGROUND OF THE INVENTION

Volatile liquid inhalation anesthestics are known in the art and include by way of example halothane, trichloroethylene, and halogenated ether derivatives including enflurane, fluroxene, methoxyflurane, isoflurane and 2-(difluoromethoxy)-1,1,1,2-tetra-fluoroethane.

The latter two inhalation anesthetics have received much attention because they provide a rapid rate of recovery and therefore are particularly suitable for administering to patients during outpatient surgery.

The most common method of preparing isoflurane ($CHF_2OCHClCF_3$) is by the reaction of trifluoroethanol ($CF_3CH_2OH$) and chlorodifluoromethane ($CF_2HCl$) in the presence of an organic base to produce a compound of the formula $CHF_2OCH_2CF_3$ which is then reacted with chlorine gas in the presence of light energy and optionally an organic solvent to thereby obtain isoflurane.

2-(difluoromethoxy)-1,1,1,2-tetrafluoroethane (hereinafter referred to as "$CHF_2OCHFCF_3$") is most commonly produced by reacting isoflurane with a fluorinating agent such as $BrF_3$. The production of $CHF_2OCHFCF_3$ is largely dependent on the starting materials used to prepare isoflurane.

The starting material, trifluoroethanol, is both difficult to produce and expensive to obtain. Use of this starting material therefore significantly increases the cost of producing both isoflurane and $CHF_2OCHFCF_3$.

It is therefore an object of the invention to provide methods of producing isoflurane and $CHF_2OCHFCF_3$ from inexpensive starting materials.

It is a further object of the invention to employ novel intermediate compounds for the production of isoflurane and $CHF_2OCHFCF_3$.

SUMMARY OF THE INVENTION

The present invention is generally directed to a process of preparing a compound of the formula $CHF_2OCHFCF_3$ from the novel starting compound dichloromethoxy—α-chloracetyl chloride (hereinafter referred to as "$CHCl_2OCHClCOCl$") and to a process in which both $CHF_2OCHFCF_3$ and isoflurane ($CHF_2OCHClCF_3$) are produced through the use of inexpensive starting materials and novel intermediates.

DETAILED DESCRIPTION OF THE INVENTION

The process of the present invention comprises reacting the novel compound $CHCl_2OCHClCOCl$ with $SF_4$ to produce the anesthetic $CHF_2OCHFCF_3$. The reaction is conducted at elevated temperatures, preferably in the range of about 145° to 155° C. Isoflurane is also produced and can be converted by known methods into $CHF_2OCHFCF_3$ for retained for use as an anesthetic.

$CHCl_2OCHClCOCl$ may be prepared by reacting $CH_3OCH_2COOH$ with a chlorinating agent such as $SOCl_2$ or $PCl_5$ to produce the corresponding acid chloride which in turn is reacted with chlorine gas in the presence of light energy either neat or in an organic solvent such as carbon tetrachloride, to produce $CHCl_2OCH_2COCl$ as a first novel intermediate compound and $CHCl_2OCHClCOCl$ as a second novel intermediate compound.

The yield of the first and second novel intermediates is temperature dependent. In general the reaction may be conducted at a temperature in the range of about $-15°$ C. to the boiling point of the solvent, or in the absence of a solvent, to about 50° C.

An increased yield of the first novel intermediate is favored by lower temperatures in the above described temperature range, preferably about 0° to 15° C., most preferably about 10° C. A higher yield of the first intermediate is desirable for the production of isoflurane ($CHF_2OCHClCF_3$).

On the other hand, for the direct production of $CHF_2OCHFCF_3$, increasing the yield of the second intermediate is desirable. Accordingly, the reaction of $CH_3OCH_2COCl$ and chlorine gas in the presence of light energy is conducted at higher temperatures than 10° C., preferably at least 20° C.

The second intermediate compound may be reacted with $SF_4$ at elevated temperatures in accordance with the invention to yield the desired compound $CHF_2OCHFCF_3$.

The first intermediate compound may be reacted with $SF_4$ at elevated temperatures to produce the isoflurane precursor $CHF_2OCH_2CF_3$, which in turn is reacted with chlorine gas and light energy, optionally in the presence of an organic solvent, to yield isoflurane. The isoflurane thus produced may be converted to $CHF_2OCHFCF_3$ by reaction with a fluorinating agent such as bromine trifluoride.

$CHF_2OCHFCF_3$ is normally a clear, colorless, liquid having the following physical properties: boiling point 23.5° C., molecular weight 168, estimated vapor pressure 660 mmHg at 20° C., and a specific gravity of 1.44. IR shows a prominent peak at 4903 cm$^{-1}$ and the $^1$H NMR shows a triplet at 6.5 ppm (J=70 Hz) and a doublet of quartets at 5.9 ppm ($J_{gem}$=56 Hz, $J_{vic}$=3 Hz). The compound is non-flammable, and stable to soda lime, rendering it particularly suitable as an inhalation anesthetic. Other characteristics and descriptions of $CHF_2OCHFCF_3$ and anesthetic compositions containing the same are disclosed in U.S. Pat. No. 4,762,856, incorporated herein by reference.

EXAMPLE 1

Production of $CHCl_2OCHClCOCl$ From Methoxy Acetyl Chloride 18.9 g of methoxy acetyl chloride ($CH_3OCH_2COCl$) and 200 ml of $CCl_4$ were added to a 300ml reactor fitted with an outer cooling jacket. The temperature of the reactor was maintained at $-5°$ to 5° C. Chlorine gas was gradually added to the reactor through a gas dispersion tube at the rate of 0.002 liter/min (0.057 mg/min).

After approximately 16 hours, the chlorine gas flow was reduced to its lowest visual setting as evidenced by the presence of bubbles in the reaction solution and continued for 8 additional hours. The reaction mass was then warmed to room temperature and the $CCl_4$ distilled off at ambient pressure. The resulting product (37.6 g) was transferred to a 50 ml flask and vacuum distilled to produce a fraction having the following characteristics:

$bp_{52mm}$=to 89° C. (10.4 g)

The $^1H$ NMR showed a 7.4 ppm singlet for $CHCl_2$—O— and a 4.6 ppm singlet for —O—$CH_2COCl$.

EXAMPLE 2

Production of $CHCl_2OCH_2ClCOCl$ From Methoxy Acetyl Chloride 20 g of methoxy acetyl chloride and 168 g of $CCl_4$ were added to the same reactor described in Example 1. The temperature of the reactor was maintained at about 30° C. Chlorine gas was gradually added to the reactor through a gas dispersion tube at approximately the same rate as described in Example 1 over approximately three hours.

The reaction mass was then allowed to warm to room temperature and the $CCl_4$ was distilled off at ambient pressure. The resulting product was vacuum distilled to produce a fraction having the following characteristics:

$bp_{2.0-4.7\ mm}$=42°-55° C. (17.2 g)

The $^1H$ NMR showed a 7.7 ppm singlet for $CHCl_2$—O— and a 5.9 ppm singlet for —O—$CH_2COCl$.

EXAMPLE 3

Reaction of $CHCl_2OCHClCOCl$ with $SF_4$

A stainless steel tube reactor containing 6.3 g (0.03 moles) of $CHCl_2OCHClCOCl$ produced in Example 1 was cooled with liquid nitrogen and 13.3 g (0.06 moles) of $SF_4$ was condensed into the stainless steel tube reactor. The reactor was warmed to room temperature and then heated to and maintained at a temperature of 145°-155° C. for 6 hours during which time the resulting pressure was from 600-650 psig.

The reactor was then cooled to room temperature and the resulting gaseous products were collected in a scrubber containing a 9% NaOH solution maintained at 10° C. The reactor was then heated to 80° C. and additional distillate collected in the NaOH scrubber. The scrubber was then heated to 100° C. to yield an organic phase which was collected in a Dean-Stark trap cooled to 0° C. Two cuts of 2.9 g and 0.5 g were collected in the trap. The cuts were analyzed by gas chromatography and found to have the following composition:

| Component | Wt (g) | Moles | % Yield |
| --- | --- | --- | --- |
| $CHF_2OCHFCF_3$ | 1.44 | 0.0086 | 29% |
| isoflurane | 1.47 | 0.0080 | 27% |

EXAMPLE 4

Reaction of $CHCl_2OCH_2COCl$ With $SF_4$

A stainless steel tube reactor containing 10.4 g (0.059 moles) of $CHCl_2OCH_2COCl$ produced in Example 2 was cooled with liquid nitrogen and 14.6 g (0.07 moles) of $SF_4$ was condensed into the tube reactor. The reactor was allowed to warm to room temperature and then gradually warmed to 132° C. over the course of 2½ hours. The pressure in the reactor increased from 95 to 505 psig.

Thereafter the temperature of the reactor was gradually raised to between 143° to 163° C. for about 1 hour causing the pressure in the reactor to increase to between 585 to 645 psi. The reactor was then maintained at a temperature between 145° to 155° C. for about 4 hours at an autogenous pressure of between 595 to 605 psig.

The reactor was then cooled to room temperature and the resulting gases were vented into a scrubber containing a solution of 50 g of 50% NaOH in 320 g of water at a temperature of −10° C.

The resulting organic layer (8.7 g) was separated from the aqueous phase. Gas chromatography showed a retention time (3.97 min) similar to that of $CF_3CH_2OCHF_2$. The product was separately tested in a mass spectropnotometer and $^1H$ NMR and the above structure was confirmed. The yield of the product was 69%. The resulting product can be readily converted to isoflurane ($CHF_2OCHClCF_3$) by reaction with chlorine gas in the presence of light energy.

What we claim is:
1. A compound of the formula $CHCl_2OCH_2COCl$.
2. A compound of the formula $CHCl_2OCHClCOCl$.

* * * * *

UNITED STATES PATENT AND TRADEMARK OFFICE
CERTIFICATE OF CORRECTION

PATENT NO. : 4,888,139
DATED : Dec. 19, 1989
INVENTOR(S) : Donald F. Halpern and Mark L. Robin It is certified that error appears in the above-identified patent and that said Letters Patent is hereby corrected as shown below:

Title Page [54], line 2, delete "$CHF_2OCHClCF_3$", and insert in place thereof -- $CHF_2OCHClCF_3$ -- .

Column 2, line 10, delete "$CHCl_2OCHlCOCl$", and insert in place thereof -- $CHCl_2OCHClCOCl$ -- ;

line 56, delete "$CHCl_2OCHClCOCl$", and insert in place thereof -- $CHCl_2OCH_2COCl$ -- .

Column 3, line 15, delete "$CHCl_2OCH_2COCl$", and insert in place thereof -- $CHCl_2OCHClCOCl$ -- ;

line 38, delete "Example 1", and insert in place thereof -- Example 2 -- .

UNITED STATES PATENT AND TRADEMARK OFFICE
CERTIFICATE OF CORRECTION

PATENT NO. : 4,888,139

DATED : Dec. 19, 1989

INVENTOR(S) : Donald F. Halpern and Mark L. Robin

Page 2 of 2

It is certified that error appears in the above-identified patent and that said Letters Patent is hereby corrected as shown below:

Column 4, line 18, delete "Example 2", and insert in place thereof -- Example 1 -- .

Signed and Sealed this

Second Day of February, 1993

Attest:

STEPHEN G. KUNIN

Attesting Officer

Acting Commissioner of Patents and Trademarks